United States Patent
Yagi et al.

(10) Patent No.: US 8,293,257 B2
(45) Date of Patent: Oct. 23, 2012

(54) OILY DISPERSION AND COSMETIC MATERIAL INCORPORATING THIS OILY DISPERSION

(75) Inventors: Kazunori Yagi, Osaka (JP); Naoki Kanda, Osaka (JP)

(73) Assignee: Tayca Corporation, Osaka (JP)

(*) Notice: Subject to any disclaimer, the term of this patent is extended or adjusted under 35 U.S.C. 154(b) by 0 days.

(21) Appl. No.: 13/338,780

(22) Filed: Dec. 28, 2011

(65) Prior Publication Data

US 2012/0100196 A1 Apr. 26, 2012

Related U.S. Application Data

(63) Continuation of application No. PCT/JP2010/061140, filed on Jun. 30, 2010.

(30) Foreign Application Priority Data

Jul. 13, 2009 (JP) ................................. 2009-165088

(51) Int. Cl.
A61K 8/04 (2006.01)
A61K 9/14 (2006.01)
A61K 33/24 (2006.01)
A61K 33/32 (2006.01)
A61K 33/26 (2006.01)
A61K 33/08 (2006.01)
A01N 59/00 (2006.01)
A01N 59/06 (2006.01)
A61K 33/00 (2006.01)

(52) U.S. Cl. ........ 424/401; 424/490; 424/617; 424/641; 424/646; 424/690; 424/691; 424/724

(58) Field of Classification Search .................. None
See application file for complete search history.

(56) References Cited

U.S. PATENT DOCUMENTS

| | | | |
|---|---|---|---|
| 4,292,087 A | 9/1981 | Bell | |
| 4,525,494 A | 6/1985 | Andy | |
| 4,563,221 A | 1/1986 | Humphreys | |
| 6,482,441 B1 * | 11/2002 | Hasegawa et al. | 424/490 |
| 2005/0147630 A1 | 7/2005 | Hasegawa et al. | |
| 2005/0197428 A1 | 9/2005 | May | |

FOREIGN PATENT DOCUMENTS

| | | |
|---|---|---|
| EP | 1 576 943 A1 | 9/2005 |
| JP | 1007941 A | 1/1989 |
| JP | 8-259432 A | 10/1996 |
| JP | 10-017849 A | 1/1998 |
| JP | 11171541 A | 6/1999 |
| JP | 11-180830 A | 7/1999 |
| JP | 2000143433 A | 5/2000 |
| JP | 2000212467 A | 8/2000 |
| JP | 2000-264823 A | 9/2000 |
| JP | 2001115058 A | 4/2001 |
| JP | 2001-200179 A | 7/2001 |
| JP | 2002-080748 A | 3/2002 |
| JP | 2004-210698 A | 7/2004 |
| JP | 2004-210730 A | 7/2004 |
| JP | 2007001867 A | 1/2007 |

OTHER PUBLICATIONS

International Search Report mailed Oct. 5, 2010 issued in a related PCT International Application No. PCT/JP2010/061140 and English translation thereof (6 pages).

* cited by examiner

*Primary Examiner* — Ernst Arnold
(74) *Attorney, Agent, or Firm* — Robert P. Michal; Lucas & Mercanti, LLP

(57) ABSTRACT

An oily dispersion of an inorganic microparticle oxide powder that exhibits excellent texture has superior compatibility with other cosmetic material components. The oily dispersion contains only two components of a dispersion medium and a surface-treated inorganic microparticle oxide powder, wherein the dispersion medium is an oil, the surface-treated inorganic microparticle oxide powder is a powder surface-treated with branched fatty acid containing isostearic acid as a primary constituent component or a metal salt containing isostearic acid as a primary constituent component at an amount of 1 to 30% by weight with respect to the powder as a base material, and the surface-treated inorganic microparticle oxide powder has a solid concentration of 25% by weight or more and a viscosity of 2,000 mPa·s or less at 25° C. in the preparation of the oily dispersion.

12 Claims, No Drawings

OILY DISPERSION AND COSMETIC MATERIAL INCORPORATING THIS OILY DISPERSION

CROSS-REFERENCE TO RELATED APPLICATION

This is a continuation of PCT International Application PCT/JP2010/061140 filed Jun. 30, 2010, which in turn claims benefit to Japanese Patent Application No. JP 2009-165088 filed Jul. 13, 2009, the entire disclosure of each of which is incorporated herein by reference.

TECHNICAL FIELD

The present invention relates to an oily dispersion and a cosmetic material containing the oily dispersion. More specifically, the present invention relates to an oily dispersion that can exhibit properties such as high solid concentration and a low viscosity by incorporating an inorganic microparticle oxide powder surface-treated with branched fatty acid containing isostearic acid as a primary constituent component or a metal salt containing isostearic acid as a primary constituent component and a cosmetic material containing the oily dispersion.

BACKGROUND ART

Inorganic microparticle powders such as microparticle titanium dioxide have been used for cosmetic materials such as sunblock in order to impart ultraviolet blocking performance in the related art.

However, when inorganic microparticle powders are mixed in the form of a powder into cosmetic materials, it is impossible to sufficiently disperse the powders with a common stirring means such as a homogenizer, a disperser and an emulsifying machine due to strong aggregation force between powders. For this reason, transparency of cosmetic materials is deteriorated, and as a result, in some cases, unnatural whitening occurs or, SPF value, which is an ultraviolet blocking indicator, cannot be sufficiently secured.

Also, when inorganic microparticle powders are mixed into cosmetic materials in the form of powders, there are problems in which handling is difficult and additional dust countermeasures are required since inorganic microparticle powder has a small particular diameter.

In this regard, dispersion is generally carried out by using a disperser having a strong stirring force such as sand grinder mill in order to further prevent aggregation between powders, or by adding silicone-based dispersing agent such as polyether modified silicone or a surfactant in order to inhibit reaggregation after dispersion and maintain dispersion stability.

Also, incorporation of a liquid dispersion obtained by previously dispersing the inorganic microparticle powders in oils such as silicone oils, ester oils, liquid paraffin or decamethylcyclopentasiloxane into cosmetic materials is carried out.

Specifically, PTL 1 discloses an oily dispersion obtained by defining an average particle diameter and a shape of microparticle titanium dioxide and using a specific organic dispersing agent, and PTL 2 discloses a method for preparing a coating composition of microparticle titanium dioxide wherein dispersion stability after dispersion is improved by adding an aluminum salt and fatty acid (salt) having 7 or more carbon atoms to an aqueous suspension of rutile-type microparticle titanium dioxide.

Further recently, microparticle titanium dioxide or oily dispersion that focuses on dispersibility of isostearic acid, for example, disclosed in PTLs 3 to 8 is developed.

Specifically, PTL 3 discloses an oily dispersion obtained by using isostearic acid and an oily solvent to a dispersion liquid of titanium alkoxide.

PTL 4 discloses microparticle titanium dioxide with superior ease of use, transparency and dispersibility by adding isostearic acid to an oily dispersion liquid and the like of titanium alkoxide, followed by coating.

PTL 5 discloses microparticle titanium dioxide in which ultraviolet protection performance can be further improved by adding isostearic acid to an oily dispersion liquid and the like of titanium alkoxide, dispersing, then removing the dispersion medium, and drying or baking.

PTL 6 discloses a microparticle titanium dioxide obtained by adding isostearic acid to an oily dispersion liquid or the like of titanium alkoxide, dispersing and then heating to the extent that the isostearic acid remains.

PTL 7 discloses an oily cosmetic material that has less aqueous stains and less stimulation in use obtained by containing microparticle titanium dioxide and isostearic acid.

PTL 8 discloses a cosmetic material slurry obtained by adding to isostearic acid and further adding polyether-modified methyl polysiloxane to microparticle titanium dioxide.

CITATION LIST

Patent Literature

PTL 1: Japanese Unexamined Patent Application Publication No. 1-7941
PTL 2: Japanese Unexamined Patent Application Publication No. 11-171541
PTL 3: Japanese Unexamined Patent Application Publication No. 2000-143433
PTL 4: Japanese Unexamined Patent Application Publication No. 2000-212467
PTL 5: Japanese Unexamined Patent Application Publication No. 2000-264823
PTL 6: Japanese Unexamined Patent Application Publication No. 2001-115058
PTL 7: Japanese Unexamined Patent Application Publication No. 2004-210730
PTL 8: Japanese Unexamined Patent Application Publication No. 2007-1867

SUMMARY OF INVENTION

Technical Problem

When the microparticle powders are dispersed in a medium such as oil, it is most preferable to make a solid concentration in the dispersion as high as possible, make the content of a dispersing agent as low as possible and reduce a viscosity of the dispersion from the viewpoint of convenience in use. Specifically, it is practically preferable that the dispersion have a high solid concentration and a viscosity of 2,000 mPa·s or less at 25° C.

Furthermore, inhibition of stability over time when used for cosmetic materials, for example, precipitation over time, or variation in viscosity over time is also required.

However, in accordance with a method using a dispersing agent represented by PTL 1, it is necessary to increase the content of dispersing agent in order to increase a solid concentration of inorganic microparticle powder. For this reason, it is difficult to make the solid concentration in the dispersion as high as possible and make the content of dispersing agent as low as possible.

Also, as described in PTL 1, 16 page, a lower section, when a dispersing agent is used for cosmetic materials, it is necessary to take into consideration stimulation of the dispersing agent on the skin and to compatibility with other components used for cosmetic materials. Accordingly, it is difficult to increase the content of the dispersing agent.

Meanwhile, the coating composition of microparticle titanium dioxide disclosed in PTL 2 advantageously maintains stability over time after dispersion and has good compatibility with other components used for cosmetic materials by coating titanium dioxide with aluminum salt.

However, the coating composition of microparticle titanium dioxide disclosed in PTL 2 has also a problem in which viscosity of the dispersion increases as solid concentration of inorganic microparticle powder increases.

Also, with regard to some of titanium dioxide microparticles and oily dispersions disclosed in PTLs 3 to 8, isostearic acid is added to a dispersion of titanium alkoxide and the surface thereof is coated with the mixture dispersion. However, isostearic acid is mainly used as a dispersing agent or an additive, and the solid concentration of such a dispersion liquid prepared by this technique is considerably low to several percentage.

As such, there is no technique in which an inorganic microparticle powder is incorporated at a high solid concentration without using any dispersing agent and a dispersion having stability over time is prepared at a low viscosity.

The present invention is made in view of the afore-mentioned problems and the present invention provides an oily dispersion that has superior compatibility with hydrocarbon-based oils such as ester oils or liquid paraffin used as cosmetic media, contains a high solid concentration of inorganic microparticle powder without using a dispersing agent and has a low viscosity and superior stability over time when the inorganic microparticle powder such as microparticle titanium dioxide having ultraviolet blocking performance is used for cosmetic materials such as sunblocks.

Also, the present invention provides cosmetic materials having ultraviolet blocking performance such as sunblocks having a high SPF vale or excellent transparency using the oily dispersion.

Solution to Problem

In order to solve the problems, an oily dispersion contains only two components of a dispersion medium and a surface-treated inorganic microparticle oxide powder, wherein the dispersion medium is an oil, the surface-treated inorganic microparticle oxide powder is a powder surface-treated with 1 to 30% by weight of the content of branched fatty acid containing isostearic acid as a primary constituent component or a metal salt containing isostearic acid as a primary constituent component with respect to the powder as a base material, and the surface-treated inorganic microparticle oxide powder has a solid concentration of 25% by weight or more and a viscosity of 2,000 mPa·s or less at 25° C. in the preparation of the oily dispersion.

Also, an average primary particle diameter of the powder as a base material may be 100 nm or less.

Also, the powder as a base material may be an oxide or a hydroxide of at least one metal selected from titanium, zinc, cerium, silicon, aluminum, iron and bismuth.

Also, the powder as a base material may be coated at an amount of 1 to 25% by weight with an aluminum compound.

Also, the content of the branched fatty acid containing isostearic acid as a primary constituent component or the metal salt containing isostearic acid as a primary constituent component may be 3 to 15% by weight.

Also, the solid concentration of the surface-treated inorganic microparticle oxide powder may be 30% by weight or more in the preparation of the oily dispersion.

Also, the oil may be at least one oil selected from esters and paraffins.

Also, provided is a cosmetic material containing the oily dispersion of the present invention.

Hereinafter, the constituent components of the present invention will be described.

The surface-treated inorganic oxide powder according to the present invention refers to a powder as a base material described below, that is, an inorganic oxide powder such as microparticle titanium dioxide whose surface is treated with branched fatty acid containing isostearic acid as a primary constituent component or a metal salt containing isostearic acid as a primary constituent component.

A powder used as a base material in the present invention is microparticle inorganic oxide having ultraviolet blocking performance such as titanium dioxide, zinc oxide, cerium oxide and bismuth oxide or microparticle inorganic oxide such as generally used for cosmetic materials anhydrous silicic acid (silicon oxide), aluminum oxide, iron oxide, and a complex thereof.

A particle diameter of the powder used as a base material in the present invention may have an average primary particle diameter in a range of 5 to 100 nm in order to sufficiently exert properties thereof. In addition, the powder more preferably has a particle diameter of 5 to 50 nm, even more preferably 5 to 30 nm.

The reason for this is that, when the average primary particle diameter is larger than 100 nm, aggregation between particles having a large particle diameter is not significant and a dispersion having a low viscosity at a high solid concentration can be obtained without using particular surface treatment, and a powder having an average primary particle diameter smaller than 5 nm is not practically applicable. Since a powder having an average primary particle diameter smaller than 5 nm does not exclude the effects of the present invention, when a powder smaller than 5 nm can be prepared, the effects of the present invention can be exerted.

Here, the average primary particle diameter is measured with a transmission electron microscope.

Specifically, the average primary particle diameter is an equivalent circle diameter obtained by dispersing a powder into a primary particle, imaging the particles with a transmission electron microscope (the number of imaging: 1,000 or more) and image-processing the imaged particles with an image analysis particle size distribution meter.

In the present invention, branched fatty acid containing isostearic acid as a primary constituent component is a product generally sold as "isostearic acid", as a commercially available product.

Isostearic acid ($C_{17}H_{35}$—COOH) is a substance that is not easily isolated into a single substance due to structure thereof. For this reason, more accurately, "isostearic acid" sold on a general market is thought to be "branched fatty acid containing isostearic acid as a primary constituent component". Accordingly, in the present invention, for more accurate expression, a product generally sold as "isostearic acid" as a commercially available product is referred to as a "branched fatty acid containing isostearic acid as a primary constituent component".

In addition, isostearic acid is not sold as a single substance on the market under the afore-mentioned circumstances. For this reason, the "branched fatty acid containing isostearic acid as a primary constituent component" may include branched fatty acid other than isostearic acid. Examples of the branched fatty acid include isopalmitic acid, isomyristic acid, dodecyl dodecanoic acid and the like. Among such branched fatty acids, branched fatty acids having 8 to 24 carbon atoms are preferred. The content ratio of isostearic acid is preferably as high as possible. Specifically, the content ratio of isostearic acid is preferably 75% by weight or more, more preferably 85% by weight or more with respect to the total amount of "branched fatty acid".

Examples of the metal salt containing isostearic acid as a primary constituent component for the present invention include aluminum isostearate, potassium isostearate, sodium isostearate and the like. In addition, similar to the afore-mentioned branched fatty acid containing isostearic acid as a primary constituent component, the metal salt containing isostearic acid as a primary constituent component used for the present invention may include metal salt of branched fatty acid other than isostearic acid.

The amount used for surface treatment of branched fatty acid containing isostearic acid as a primary constituent component or metal salt containing isostearic acid as a primary constituent component is preferably 1 to 30% by weight, more preferably 3 to 15% by weight, with respect to the amount of the powder as a base material.

When the amount used for surface treatment is higher than 30% by weight, the powder is aggregated, and thus it becomes difficult to disperse the powder. Although there is no problem associated with performance in an amount of surface treatment of lower than 30% by weight, from the viewpoint of ultraviolet blocking, the larger the amount of inorganic powder contained in an oily dispersion, that is, the smaller the amount of surface treatment, the more preferable it is.

For example, a method of surface treatment used for the present invention is carried out by forming a metal soap on the surface of a powder as a base material while adjusting pH of the powder as the base material in an aqueous dispersion. Also, the surface treatment may be carried out by stirring and mixing microparticle titanium dioxide with branched fatty acid containing isostearic acid as a primary constituent component in an organic solvent, and distilling the organic solvent, followed by heating.

When surface treatment is carried out using branched fatty acid containing isostearic acid as a primary constituent component, for example, a powder used as a base material may be coated with an inorganic oxide or hydroxide of aluminum or the like in order to improve light resistance of powder as a base material or inhibit reactivity with other substances.

For example, the coating treatment method may be carried out by dispersing microparticle titanium dioxide, a powder as a base material in an aqueous dispersion, dissolving an aqueous salt of an inorganic oxide or hydroxide of aluminum or the like for coating therein, and depositing a coating substance such as aluminum hydroxide on the surface of the powder while adjusting pH.

At this time, the branched fatty acid containing isostearic acid as a primary constituent component together with an aqueous salt of inorganic oxide or hydroxide of aluminum or the like for coating may be mixed with a water dispersion of the powder as a base material, or mixed after dissolving the aqueous salt of inorganic oxide or hydroxide of aluminum or the like for coating, followed by coating.

Also, when the metal salt containing isostearic acid as a primary constituent component such as aluminum isostearate is used, the same effects as the afore-mentioned coating can be obtained without performing the corresponding treatment during surface treatment.

The ratio of inorganic oxide or hydroxide used as a substance for coating the powder as a base material during the coating is preferably 1 to 25% by weight, more preferably 2 to 15% by weight, in terms of oxide. When the ratio is lower than 1%, improvement in light resistance or inhibition of reactivity is sufficiently not exerted and when the ratio is higher than 25%, the ratio of base substance powder such as microparticle titanium dioxide in the oily dispersion decreases, ultraviolet blocking performance is deteriorated and coating effects are limited.

Examples of the dispersion medium in the present invention include hydrocarbons such as squalene, liquid paraffin, light liquid isoparaffin, medium liquid isoparaffin, microcrystalline waxes and solid paraffin, silicones such as dimethicone, phemethicone, cyclomethicone, decamethylcyclopentasiloxane, esters such as jojoba oil, carnauba wax, Japanese wax, beeswax, spermaceti, octyl dodecyl oleate, isopropyl myristate, neopentyl glycol diisostearate, diisostearyl malate, isononyl isononanoate, isotridecyl isononanoate, fatty acids such as stearic acid, lauric acid, myristic acid, palmitic acid, isostearic acid, isopalmitic acid, behenic acid and oleic acid, higher alcohols such as such as behenyl alcohol, cetanol, oleyl alcohol, octadecyl alcohol, triglycerides such as castor oil, coconut oil, hydrogenated castor oil, Cedrela sinensio oil, wheat germ oil, trigylceryl isostearate, isookutanoic acid trigylceryl, olive oil, and polyvalent alcohols such as 1,3-butanediol, glycerine, diglycerine, dipropylene glycol, polyethylene glycol, 1,2-pentanediol, 1,2-hexyleneglycol, isoprene glycol.

In addition, the dispersion medium may be used alone or in combination thereof.

Of these, hydrocarbons such as liquid paraffin, esters such as isononyl isononanoate, and silicones such as decamethylcyclopentasiloxane are preferred.

The content (medium concentration) of the dispersion medium in the present invention is preferably 35 to 75% by weight, more preferably 40 to 70% by weight, with respect to the total amount of the oily dispersion of the present invention.

Accordingly, the content (solid concentration) of the inorganic microparticle oxide powder surface-treated with branched fatty acid containing isostearic acid as a primary constituent component or the like in the oily dispersion of the present invention is preferably 25 to 65% by weight, more preferably 30 to 60% by weight.

In addition, the viscosity of oily dispersion of the present invention is preferably 2,000 mPa·s or less at 25° C. due to the contents of the two components.

The cosmetic material of the present invention may optionally contain, in addition to the oily dispersion of the present invention, commonly used various components for cosmetic materials. Examples of these components include, in addition to the various oils, organic powders (also, the powder surface of these components may be treated with a coupling agent, an inorganic compound or the like with the proviso that the application thereof is not impaired) such as crystalline cellulose, cross-linked methylpolysiloxane, polyethylene powder and acrylic resin powders, inorganic powders such as talc, mica, sericite, magnesium carbonate, calcium carbonate, titanium dioxide, iron oxide, Prussian blue, Ultramarine blue, mica titanium, sericite titanium, silica, alkyl acylate/methacrylate copolymer and/or salts thereof, carboxyvinyl polymers and/or salts thereof, a thickening agent such as xanthan gum or hydroxypropyl cellulose, vitamins such as retinol, retinoic acid, tocopherol, riboflavin, pyridoxine, ascorbic acid, and ascorbate phosphate ester, terpenes such as glycyrrhizate, glycyrrhizin, ursolic acid and oleanolic acid, steroids such as estra diol, ethynylestradiol, erythritol, preservatives such as phenoxy ethanol, parabens, hibitane gluconate and benzalkonium chloride, ultraviolent absorbers such as dimethylaminobenzoic acid esters, cinnamic acid esters and benzophenones and the like.

The application of the oily dispersion of the present invention is not particularly limited and preferred applications thereof include cosmetic materials such as sunblocks. Also, the oily dispersion may be also used for ultraviolet blocking materials such as foundation or base make-up.

Advantageous Effects of Invention

As mentioned above, according to the present invention, by using branched fatty acid containing isostearic acid as a primary constituent component or metal salt containing isostearic acid as a primary constituent component, as a surface treating agent of an inorganic oxide powder such as titanium dioxide, an oily dispersion that has superior compatibility with hydrocarbon-based oils such as ester oils or liquid paraffin and has a high solid concentration and a low viscosity of 2,000 mPa·s or less without adding a dispersing agent can be obtained.

In addition, the aforementioned effects from microparticle inorganic oxide having an average primary particle diameter of 100 nm or less can be obtained.

Also, the aforementioned effects can be obtained from most inorganic oxide generally used for cosmetic materials.

Also, by previously coating a powder as a base material with an aluminum compound, the aforementioned effects can be further obtained and light resistance of the powder as a base material can be improved or reactivity thereof with other substances can be inhibited.

When the oily dispersion of the present invention is used for cosmetic materials having ultraviolet blocking performance such as sunblocks, since the obtained cosmetic material uses highly safe hydrocarbon-based oils such as ester oils or liquid paraffin, the oily dispersion has excellent compatibility with other cosmetic material components and has a high solid concentration, a low viscosity and superior stability over time, furthermore, cosmetic materials having soft texture and cosmetic materials such as sunblocks having high SPF value or transparency can be prepared.

DESCRIPTION OF EMBODIMENTS

Then, the oily dispersion of the present invention and cosmetic material will be described in detail based on the specific examples. In addition, the present invention is not limited to the following examples.

Examples 1 to 3

(1) Process 1

4,000 g of a 48% caustic soda solution was added to 3,500 g of a purified water-containing microparticle titanium dioxide cake (corresponding to 1,000 g in terms of $TiO_2$) with stirring, followed by further stirring at 95° C. to 105° C. for two hours. Subsequently, the resulting microparticle titanium dioxide hydrate was sufficiently washed and the cake was obtained as a slurry. In addition, 1,400 g of 35% hydrochloric acid was added with stirring, and the mixture was aged at 95° C. for two hours to obtain a slurry (the resulting slurry had a crystalline structure of rutile-type titanium dioxide when observed by X-ray diffraction).

The titanium dioxide slurry thus obtained was adjusted to a concentration of 70 g/liter.

A powder image was read from a transmission electron microscope image of titanium dioxide slurry thus obtained using a particle size distribution measurement software for image analysis (Mac-View: manufactured by MOUNTECH Co., Ltd.), and shape data such as particle size distribution was calculated. As a result, an average primary particle diameter was 15 nm.

(2) Process 2

10 liters (corresponding to 700 g in terms of $TiO_2$) of the slurry obtained in the process 1 was heated at 85° C., 508 ml of a polyaluminum chloride solution (9% by weight in terms of $Al_2O_3$, based on titanium dioxide) was added thereto with stirring to adjust the pH value to 5.5 and the mixture was aged for 30 minutes. Then, the pH value was adjusted to 9.0 and 77 g (11% by weight in terms of fatty acid, based on titanium dioxide) of isostearic acid (isostearic acid EX manufactured by Kokyu Alcohol Kogyo Co., Ltd.) was added thereto. At this time, the pH value was slowly decreased and reached about 8.0 for 30 minutes. After aging for one hour, the pH value was adjusted to 7.0, the reaction mixture was aged for 30 minutes and the pH value was adjusted again to 5.0 to surface-treat titanium dioxide dispersion particles with isostearic acid. Then, after further aging for 30 minutes, the solid was filtered, washed and dried at 85° C. for 15 hours. The resulting dried matter was ground with an egg atomizer.

(3) Process 3

350 g of a dispersion medium was mixed with 150 g of the dried and ground matter obtained in the process 2 as a surface-treated inorganic microparticle oxide powder with stirring, followed by wet dispersion in a sand grinder mill (using 0.5 mm zirconia beads) to obtain respective oily dispersions.

Also, alkyl benzoate (C12-15), liquid paraffin and decamethylcyclopentasiloxane were used as dispersion media. All the dispersion media had a solid concentration of 30%.

(4) Analysis of Product

The Oil absorption of dried and ground matter obtained in the process 2 (microparticle titanium dioxide treated with isostearic acid and aluminum hydroxide) and the viscosity of oily dispersions obtained in the process 3 were measured. The measurement results of Oil absorption are shown in Table 1 and the measurement results of viscosity of oily dispersion are shown in Table 2.

Also, various measurement conditions are given as follows.
Oil Absorption
  Measured in accordance with JIS K 5101-13-2.
Viscosity
  Measurement conditions: B-type viscosity meter at 6 rpm and 25° C.

Comparative Examples 1 to 3

The Oil absorption and the viscosity of oily dispersions of dried and ground matters obtained by performing the processes 1 to 3 of Example 1 using stearic acid (purified stearic acid 550V manufactured by Kao Corporation), instead of isostearic acid used for the process 2 of Example 1 were measured. The measurement results of oil absorption are shown in Table 1 and measurement results of the viscosity of oily dispersion are shown in Table 2.

TABLE 1

| | Oil absorption (g/100 g) | |
|---|---|---|
| | Boiled linseed oil | Decamethylcyclopentasiloxane |
| Dried and ground matter obtained in the process 2 of Example 1 | 23 | 27 |
| Dried and ground matter obtained in the process 2 of Comparative Example 1 | 30 | 34 |

TABLE 2

| | Dispersion medium | Viscosity (mPa·s) |
|---|---|---|
| Example 1 | Alkyl benzoate (C12-15) | 1,500 |
| Comparative Example 1 | | 3,000 |
| Example 2 | Liquid paraffin | 1,400 |
| Comparative Example 2 | | 10,000 |
| Example 3 | Decamethylcyclopentasiloxane | 500 |
| Comparative Example 3 | | 5,000 |

Examples 4 to 11

(1) Process 1

11,000 g of a 48% caustic soda solution was added to 3,500 g of a purified water-containing microparticle titanium dioxide cake (corresponding to 1,000 g in terms of $TiO_2$) with stirring, followed by further stirring at 95° C. to 105° C. for two hours. Subsequently, the resulting microparticle titanium dioxide hydrate was sufficiently washed and the cake was obtained as a slurry. In addition, 3,000 g of 35% hydrochloric acid was added with stirring, and the mixture was aged at 95° C. for two hours to obtain a slurry (the resulting slurry had a crystalline structure of rutile-type titanium dioxide when observed by X-ray diffraction).

The titanium dioxide slurry thus obtained was adjusted to a concentration of 70 g/liter.

A powder image was read from a transmission electron microscope image of titanium dioxide slurry thus obtained using a particle size distribution measurement software for image analysis (Mac-View: manufactured by MOUNTECH Co., Ltd.), and shape data such as particle size distribution was calculated. As a result, an average primary particle diameter was 10 nm.

(2) Process 2

10 liters (corresponding to 700 g in terms of $TiO_2$) of the slurry obtained in the process 1 was heated to 85° C., 847 ml of a polyaluminum chloride solution (15% by weight in terms of $Al_2O_3$, based on titanium dioxide) was added thereto with stirring to adjust the pH value to 5.5 and the mixture was aged for 30 minutes. Then, the pH value was adjusted to 9.0 and 91 g (13% by weight in terms of fatty acid, based on titanium dioxide) of isostearic acid (isostearic acid EX manufactured by Kokyu Alcohol Kogyo Co., Ltd.) was added thereto. At this time, the pH value was slowly decreased and reached about 8.0 for 30 minutes. After aging for one hour, the pH value was adjusted to 7.0, the reaction mixture was aged for 30 minutes and the pH value was adjusted again to 5.0 to surface-treat titanium dioxide dispersion particles with isostearic acid. Then, after further aging for 30 minutes, the solid was filtered, washed and dried at 85° C. for 15 hours. The resulting dried matter was ground with an egg atomizer.

(3) Process 3

The dried and ground matter (average primary particle diameter of 15 nm) prepared in the processes 1 and 2 of Example 1 was defined as a "treated powder A" and the dried and ground matter (average primary particle diameter of 15 nm) prepared in the processes 1 and 2 of Example 4 was defined as a "treated powder B", and dispersions of the respective treated powders in different dispersion media were prepared under the following preparation conditions and the viscosity immediately after preparation and viscosity at 50° C. after one month were measured and stability over time was confirmed. Also, SPF was measured. The results are shown in Table 3.

Preparation conditions

Disperser: Paint conditioner

Container: 100 ml polymeric container

Beads: 1.5 mmφ glass bead, addition amount of 50 g

Dispersion time: 60 min.

Mixing composition: treated powder/dispersion medium=30/70 or 40/60

Viscosity measurement conditions: viscosity was measured using a B-type viscosity meter at 60 rpm and 25° C., immediately after preparation and at 50° C. after one month. SPF measurement conditions: Measuring apparatus/Labsphere UV1000S, Base/Vitro-Skin Lot#7009, coated amount/2.0 mg/cm$^2$ Comparative Examples 4 to 15

The dried and ground matter (average primary particle diameter of 15 nm) prepared in the processes 1 and 2 of Comparative Example 1 was defined as a "treated powder C" and the dried and ground matter (average primary particle diameter of 10 nm) prepared in the same manner as in Example 4, except that stearic acid was relatively used for surface treatment instead of isostearic acid in the process 2 of Example 4 was defined as a "treated powder D", a powder obtained by treating microparticle titanium dioxide having an average primary particle diameter of 10 nm with water-containing silicic acid and aluminum hydroxide and further treating the same with a (dimethicone/methicone) copolymer was defined as a "treated powder E", dispersions of the respective treated powders in different dispersion media were prepared under the following preparation conditions, a viscosity immediately after preparation and a viscosity at 50° C. after one month were measured and stability over time was confirmed. Also, SPF was measured. The results are shown in Table 3.

TABLE 3

| | Treated powder | Dispersion medium | Powder concentration (%) | Medium concentration (%) | Viscosity (25° C.)(mPa·s) Immediately after preparation | Viscosity (25° C.)(mPa·s) 50° C. and after one month | SPF |
|---|---|---|---|---|---|---|---|
| Example 4 | A | Squalene | 30 | 70 | 600 | 600 | 48 |
| Example 5 | B | | 30 | 70 | 900 | 1,000 | 45 |
| Comparative Example 4 | C | | 30 | 70 | 10,000 or higher | 10,000 or higher | 45 |
| Comparative Example 5 | D | | 30 | 70 | 10,000 or higher | 10,000 or higher | 40 |
| Comparative Example 6 | E | | 30 | 70 | 10,000 or higher | 10,000 or higher | 24 |
| Example 6 | A | Isononyl isononanoate | 30 | 70 | 200 | 200 | 65 |
| Example 7 | B | | 30 | 70 | 250 | 300 | 55 |
| Comparative Example 7 | C | | 30 | 70 | 2,500 | 6,000 | 56 |
| Comparative Example 8 | D | | 30 | 70 | 4,000 | 10,000 or higher | 42 |
| Comparative Example 9 | E | | 30 | 70 | 5,000 | 10,000 or higher | 38 |
| Example 8 | A | Isotridecyl isononanoate | 30 | 70 | 900 | 900 | 55 |
| Example 9 | B | | 30 | 70 | 1,200 | 1,200 | 52 |
| Comparative Example 10 | C | | 30 | 70 | 10,000 or higher | 10,000 or higher | 46 |
| Comparative Example 11 | D | | 30 | 70 | 10,000 or higher | 10,000 or higher | 46 |
| Comparative Example 12 | E | | 30 | 70 | 10,000 or higher | 10,000 or higher | 18 |
| Example 10 | A | Liquid paraffin | 40 | 60 | 70 | 80 | 88 |
| Example 11 | B | | 30 | 70 | 500 | 450 | 74 |
| Comparative Example 13 | C | | 40 | 60 | 3,500 | 8,000 | 68 |
| Comparative Example 14 | D | | 30 | 70 | 5.000 | 10,000 or higher | 56 |
| Comparative Example 15 | E | | 30 | 70 | 5,000 | 10,000 or higher | 21 |

Examples 12 and 13

Three components, that is, 20 g of "treated powder A" or "treated powder B" prepared in Examples 4 to 11 as a treated powder, 30 g of squalene and 10 g of isononyl isononanoate were mixed with one another to obtain a dispersion using a paint conditioner under the conditions of Examples 4 to 11. A cosmetic material was prepared in accordance with the following prescription using 30 g of the obtained dispersion (containing 10 g of treated powder, 15 g of squalene and 5 g of isononyl isononanoate as mentioned below), viscosity and SPF were measured, and function tests were measured in terms of transparency and ease of use (spreadability). The results are shown in Table 4.

Mixing
Oil phase:

| Treated powder | 10 g |
|---|---|
| Squalene | 15 g |
| Isononyl isononanoate | 5 g |
| Cetyl palmitate | 3 g |
| dimethicone | 2 g |
| Decaglyceryl monostearate | 2 g |
| Behenyl alcohol | 1.5 g |
| Glyceryl monostearate | 1 g |
| Stearic acid | 1 g |

Preservative Appropriate amount
Aqueous phase:

| Water | About 57 g |
|---|---|
| Butylene glycol | 5 g |
| xanthan gum | 0.1 g |
| Potassium hydroxide | 0.1 g |

Preservative appropriate amount

Emulsification conditions: homogenizer, 3,000 rpm, 10 min.

Viscosity measurement conditions: B-type viscosity meter 60 rpm and 25° C.

SPF measurement conditions:
   Measuring apparatus/Labsphere UV1000S,
   Base/Vitro-Skin Lot#7009, coated amount/2.0 mg/cm$^2$ Comparative Examples 16 to 18

The "treated powder C", "treated powder D", "treated powder E" prepared in Comparative Examples 4 to 15 were subjected to measurement tests in terms of viscosity, SPF value, transparency and ease of use (spreadability) in the same manner as Examples 12 and 13, respectively.

The results are shown in Table 4. In addition, the results of function tests in terms of transparency and ease of use were evaluated by 5 monitors based on 5-grade (bad: 1, slightly bad: 2, medium: 3, slightly good: 4, good: 5) and an average ≦4 was represented by ⊙, 2≦an average <4 was represented by ○, and an average <2 was represented by Δ.

TABLE 4

|  | Example 12 | Example 13 | Comparative Example 16 | Comparative Example 17 | Comparative Example 18 |
|---|---|---|---|---|---|
| Treated powder | A | B | C | D | E |
| Viscosity (25° C.) (mPa · s) | 600 | 800 | 4,000 | 6,000 | 5,000 |
| SPF value | 28 | 22 | 21 | 19 | 7 |
| Transparency (evaluated by the naked eye) | ○ | ⊙ | Δ | ○ | ○ |
| Ease of use (spreadability) | ⊙ | ⊙ | Δ | ○ | ○ |

Examples 14 to 16

1,000 g of titanium dioxide (MT-700B manufactured by Teika Pharmaceutical Co., Ltd.: average primary particle diameter of 80 nm) was mixed with 10 liters of water with stirring, the mixture was heated to 85° C., 160 ml of a polyaluminum chloride solution (2% by weight in terms of $Al_2O_3$, based on titanium dioxide) was added thereto with stirring, the pH value was adjusted to 5.5, and the mixture was aged for 30 minutes. Then, the pH value was adjusted to 9.0, 40 g (4% by weight in terms of fatty acid, based on titanium dioxide) of isostearic acid (isostearic acid EX manufactured by Kokyu Alcohol Kogyo Co., Ltd.) was added thereto.

At this time, the pH value was slowly decreased and reached about 8.0 for 30 minutes. After aging for one hour, the pH value was adjusted to 7.0, the reaction mixture was aged for 30 minutes and the pH value was adjusted again to 5.0 to surface-treat titanium dioxide dispersion particles with isostearic acid. Then, after further aging for 30 minutes, the solid was filtered, washed and dried at 85° C. for 15 hours. The resulting dried matter was ground with an egg atomizer.

A dispersion was prepared under the following conditions using the resulting powder and viscosity was measured. The measurement results are shown in Table 5.
Dispersion medium: isononyl isononanoate, isotridecyl isononanoate, liquid paraffin
Mixing composition: treated powder/dispersion medium=30/70
Dispersion conditions: DISPER (T. K. Robomix manufactured by primix Co., Ltd.) 3,000 rpm and for 5 min.
Measurement conditions: B-type viscosity meter at 6 rpm and 25° C., immediately after preparation

TABLE 5

|  | Dispersion medium | Viscosity (25° C.) (mPa · s) |
|---|---|---|
| Example 4 | Isononyl isononanoate | 1,310 |
| Example 15 | Isotridecyl isononanoate | 2,000 |
| Example 16 | Liquid paraffin | 400 |

Examples 17 to 22

3,000 g of microparticle zinc oxide (MZ-500 manufactured by Teika Pharmaceutical Co., Ltd.: average primary particle diameter of 25 nm) was mixed with 300 g of isostearic acid (isostearic acid EX manufactured by Kokyu Alcohol Kogyo Co., Ltd.) in 6,000 g of isopropanol with stirring, followed by wet dispersion in a sand grinder mill and separation of isopropanol with a vacuum kneader. The resulting dried matter was heated at 120° C. for 5 hours and was ground with an egg atomizer.

The viscosity of the dispersion of microparticle zinc oxide surface-treated with the isostearic acid obtained in the process using the following medium was measured.

The viscosity was measured immediately after preparation and at 50° C. after one month, stability over time was confirmed. The various conditions are given as follows. The results are shown in Table 6.
Dispersion medium: squalene, isononyl isononanoate, isotridecyl isononanoate, triethylhexanoin, liquid paraffin, decamethylcyclopentasiloxane
Mixing compositio: treated powder/dispersion medium=40/60
Dispersion conditions: DISPER, at 3,000 rpm and for 10 min.
Measurement conditions: viscosity was measured using a B-type viscosity meter at 6 rpm and 25° C., immediately after preparation and at 50° C. after one month.

Comparative Examples 19 to 24

Also, the viscosity of a dispersion prepared in the same manner except that stearic acid (purified stearic acid 550V manufactured by Kao Corporation) was used instead of isostearic acid used in Examples 17 to 22 above was measured. The results are shown in Table 6.

TABLE 6

|  |  | Viscosity (25° C.) (mPa · s) | |
|---|---|---|---|
|  | Dispersion medium | Immediately after preparation | At 50° C. and after one month |
| Example 17 | squalene | 1,600 | 1,500 |
| Comparative Example 19 |  | 10,000 or higher | 10,000 or higher |
| Example 18 | Isononyl isononanoate | 1,200 | 1,300 |
| Comparative Example 20 |  | 10,000 or higher | 10,000 or higher |
| Example 19 | Isotridecyl isononanoate | 1,600 | 1,600 |
| Comparative Example 21 |  | 10,000 or higher | 10,000 or higher |
| Example 20 | Triethylhexanoin | 1,500 | 1,500 |
| Comparative Example 22 |  | 10,000 or higher | 10,000 or higher |
| Example 21 | Liquid paraffin | 200 | 250 |
| Comparative Example 23 |  | 4,000 | 7,000 |
| Example 22 | Decamethylcyclopentasiloxane | 900 | 900 |
| Comparative Example 24 |  | 8,000 | 1,500 |

Examples 23 to 28, Comparative Examples 25 to 30

The viscosity of oily dispersions prepared using respective dispersion media in the same manner as in Example 17 except that cerium oxide (Seri guard W-500 manufactured by DAITO Pharmaceutical Co., Ltd.: primary particle diameter of 10 to 25 nm) was used instead of microparticle zinc oxide of Example 17 was measured.

In addition, the viscosity of oily dispersions, as Comparative Examples 25 to 30, prepared using stearic acid instead of isostearic acid of Examples 23 to 28 was measured.

The viscosity measurement conditions are the same as in Example 17 except that the mixing ratio was set at treated powder:dispersion medium=35:65. The results are shown in Table 7.

TABLE 7

| | Dispersion medium | Viscosity (25° C.) (mPa · s) |
|---|---|---|
| Example 23 | Squalene | 1,300 |
| Comparative Example 25 | | 10,000 or higher |
| Example 24 | Isononyl isononanoate | 1,000 |
| Comparative Example 26 | | 10,000 or higher |
| Example 25 | Isotridecyl isononanoate | 1,300 |
| Comparative Example 27 | | 10,000 or higher |
| Example 26 | Triethylhexanoin | 1,200 |
| Comparative Example 28 | | 10,000 or higher |
| Example 27 | Liquid paraffin | 200 |
| Comparative Example 29 | | 4,000 |
| Example 28 | Decamethylcyclopentasiloxane | 700 |
| Comparative Example 30 | | 7,000 |

Examples 29 to 34, Comparative Examples 31 to 36

The viscosity of oily dispersions prepared using respective dispersion media in the same manner as in Example 17 except that silica (AEROSIL 130 manufactured by Nippon Aerosil Co., ltd.: average primary particle diameter of 18 nm) was used instead of microparticle zinc oxide of Example 17 was measured.

In addition, the viscosity of oily dispersions, as Comparative Examples 31 to 36, prepared using stearic acid instead of isostearic acid of Examples 29 to 34 was measured.

The viscosity measurement conditions are the same as in Example 17 except that mixing composition was set at treated powder:dispersion medium=25:75. The results are shown in Table 8.

TABLE 8

| | Dispersion medium | Viscosity (25° C.) (mPa · s) |
|---|---|---|
| Example 29 | Squalene | 1,900 |
| Comparative Example 31 | | 10,000 or higher |
| Example 30 | Isononyl isononanoate | 1,600 |
| Comparative Example 32 | | 10,000 or higher |
| Example 31 | Isotridecyl isononanoate | 1,900 |
| Comparative Example 33 | | 10,000 or higher |
| Example 32 | Triethylhexanoin | 1,700 |
| Comparative Example 34 | | 10,000 or higher |
| Example 33 | Liquid paraffin | 500 |
| Comparative Example 35 | | 6,000 |
| Example 34 | Decamethylcyclopentasiloxane | 1,000 |
| Comparative Example 36 | | 9,000 |

Examples 35 to 40, Comparative Examples 37 to 42

The viscosity of oily dispersions prepared using respective dispersion media in the same manner as in Example 17 except that aluminum oxide (Aluminum Oxide C manufactured by Nippon Aerosil Co., ltd.: average primary particle diameter of 13 nm) was used instead of microparticle zinc oxide of Example 17 was measured.

In addition, the viscosity of oily dispersions, as Comparative Examples 37 to 42, prepared using stearic acid instead of isostearic acid of Examples 35 to 40 was measured.

The viscosity measurement conditions are the same as in Example 17 except that the mixing composition was set at treated powder:dispersion medium=25:75. The results are shown in Table 9.

TABLE 9

| | Dispersion medium | Viscosity (25° C.) (mPa · s) |
|---|---|---|
| Example 35 | Squalene | 1,800 |
| Comparative Example 37 | | 10,000 or higher |
| Example 36 | Isononyl isononanoate | 1,500 |
| Comparative Example 38 | | 10,000 or higher |
| Example 37 | Isotridecyl isononanoate | 1,800 |
| Comparative Example 39 | | 10,000 or higher |
| Example 38 | Triethylhexanoin | 1,700 |
| Comparative Example 40 | | 10,000 or higher |
| Example 39 | Liquid paraffin | 400 |
| Comparative Example 41 | | 5,000 |
| Example 40 | Decamethylcyclopentasiloxane | 900 |
| Comparative Example 42 | | 8,000 |

Examples 41 to 46, Comparative Examples 43 to 48

The viscosity of oily dispersions prepared using respective dispersion media in the same manner as in Example 17 except that iron oxide (R-516P manufactured by Titan Kogyo Co., Ltd.: average primary particle diameter of 75 nm) was used instead of microparticle zinc oxide of Example 17 was measured.

In addition, the viscosity of oily dispersions, as Comparative Examples 43 to 48, prepared using stearic acid instead of isostearic acid of Examples 41 to 46 was measured.

The viscosity measurement conditions are the same as in Example 17 except that the mixing composition was set at treated powder:dispersion medium=50:50. The results are shown in Table 10.

TABLE 10

| | Dispersion medium | Viscosity (25° C.) (mPa·s) |
|---|---|---|
| Example 41 | Squalene | 900 |
| Comparative Example 43 | | 10,000 |
| Example 42 | Isononyl isononanoate | 700 |
| Comparative Example 44 | | 8,000 |
| Example 43 | Isotridecyl isononanoate | 900 |
| Comparative Example 45 | | 9,000 |
| Example 44 | Triethylhexanoin | 800 |
| Comparative Example 46 | | 8,000 |
| Example 45 | Liquid paraffin | 200 |
| Comparative Example 47 | | 4,000 |
| Example 46 | Decamethylcyclopentasiloxane | 500 |
| Comparative Example 48 | | 5,000 |

Examples 47 to 52, Comparative Examples 49 to 54

66.6 g of water and 11.3 g of 61% nitric acid were added to a beaker, followed by mixing, and 24.3 g of bismuth nitrate pentahydrate (manufactured by Sigma Aldrich Corp) was added to the mixture solution, followed by dissolution to obtain an aqueous acidic solution of bismuth nitrate. Separately, a 24% aqueous sodium hydroxide solution was prepared.

Then, 150 g of water was added to a 1 liter container, followed by heating to 50° C. The aqueous acidic solution of bismuth nitrate and the 24% aqueous sodium hydroxide solution were simultaneously added portionwise thereto while maintaining pH 10, to perform hydrolysis of bismuth. The addition of aqueous acidic solution of bismuth nitrate and the 24% aqueous sodium hydroxide solution was carried out by dropwise addition using a roller pump. The addition was carried out at pH 10 over about 30 minutes at an addition ratio such that sodium hydroxide was about 4 equivalents with respect to one equivalent of bismuth.

A precipitate produced by hydrolysis was filtered, washed, dried at 110° C. for 3 hours and baked in an electric furnace at 550° C. for two hours.

1,000 g of bismuth oxide obtained by repeating the operation several times was mixed with 100 g of isostearic acid in 2,500 g of isopropanol with stirring, followed by wet dispersion in a sand grinder mill (rotation treatment for 12 hours) to perform micronization, and separation of isopropanol with a vacuum kneader. The resulting dried matter was heated at 120° C. for 5 hours and ground with an egg atomizer. The average primary particle diameter of obtained bismuth oxide was measured and then obtained as 20 nm.

The viscosity of oily dispersions prepared using the obtained treated powder and respective dispersion media in the same manner as in Example 17 was measured. The viscosity measurement conditions are the same as in Example 17.

In addition, the viscosity of oily dispersions, as Comparative Examples 49 to 54, prepared using stearic acid instead of isostearic acid of Examples 47 to 52 was measured.

The results thus obtained are shown in Table 11.

TABLE 11

| | Dispersion medium | Viscosity (25° C.) (mPa·s) |
|---|---|---|
| Example 47 | Squalene | 1,500 |
| Comparative Example 49 | | 10,000 or higher |
| Example 48 | Isononyl isononanoate | 1,100 |
| Comparative Example 50 | | 10,000 or higher |
| Example 49 | Isotridecyl isononanoate | 1,500 |
| Comparative Example 51 | | 10,000 or higher |
| Example 50 | Triethylhexanoin | 1,400 |
| Comparative Example 52 | | 10,000 or higher |
| Example 51 | Liquid paraffin | 300 |
| Comparative Example 53 | | 4,000 |
| Example 52 | Decamethylcyclopentasiloxane | 300 |
| Comparative Example 54 | | 8,000 |

As apparent from the fore-going, according to the present invention, by using branched fatty acid containing isostearic acid as a primary constituent component or metal salt containing isostearic acid as a primary constituent component, as a surface treating agent of an inorganic oxide powder such as titanium dioxide, an oily dispersion that has superior compatibility with hydrocarbon-based oils such as ester oils or liquid paraffin and has a high solid concentration and a low viscosity of 2,000 mPa·s or less without adding a dispersing agent can be obtained.

In addition, when the oily dispersion of the present invention is used for cosmetic materials having ultraviolet blocking performance such as sunblocks, since the obtained cosmetic material uses highly stable hydrocarbon-based oils such as ester oils or liquid paraffin, the oily dispersion has excellent compatibility with other cosmetic material components and has a high solid concentration, a low viscosity and superior stability over time, and furthermore, cosmetic materials having soft texture and cosmetic materials such as sunblocks having high SPF value or transparency can be prepared.

The invention claimed is:

1. An oily dispersion comprising only two components of a dispersion medium and a surface-treated inorganic microparticle oxide powder,
   wherein the dispersion medium is an oil,
   the surface-treated inorganic microparticle oxide powder is a powder surface-treated with branched fatty acid containing isostearic acid as a primary constituent component or a metal salt containing isostearic acid as a primary constituent component at an amount of 3 to 15% by weight with respect to the powder as a base material, and is powder surface-treated using isopropanol or by wet dispersion with a water-soluble salt of aluminum oxide or a water-soluble salt of aluminum hydroxide; and
   the surface-treated inorganic microparticle oxide powder has a solid concentration of 25% by weight or more and a viscosity of 2,000 mPa·s or less at 25° C. in the preparation of the oily dispersion.

2. The oily dispersion according to claim 1, wherein an average primary particle diameter of the powder as a base material is 100 nm or less.

3. The oily dispersion according to claim 1, wherein the powder as a base material is oxide or hydroxide of at least one metal selected from titanium, zinc, cerium, silicon, aluminum, iron and bismuth.

4. The oily dispersion according to claim 1, wherein the powder as a base material is coated at an amount of 1 to 25% by mass with an aluminum compound.

5. The oily dispersion according to claim 1, wherein the content of the branched fatty acid containing isostearic acid as a primary constituent component or the metal salt containing isostearic acid as a primary constituent component is 3 to 15% by mass.

6. The oily dispersion according to claim 1, wherein the solid concentration of the surface-treated inorganic microparticle oxide powder is 30% by mass or more in the preparation of the oily dispersion.

7. The oily dispersion according to claim 1, wherein the oil is at least one oil selected from esters and paraffins.

8. A cosmetic material comprising the oily dispersion according to claim 1.

9. The oily dispersion according to claim 4, wherein the content of the branched fatty acid containing isostearic acid as a primary constituent component or the metal salt containing isostearic acid as a primary constituent component is 3 to 15% by mass.

10. The oily dispersion according to claim 4, wherein the solid concentration of the surface-treated inorganic microparticle oxide powder is 30% by mass or more in the preparation of the oily dispersion.

11. The oily dispersion according to claim 4, wherein the oil is at least one oil selected from esters and paraffins.

12. A cosmetic material comprising the oily dispersion according to claim 4.

* * * * *